(12) United States Patent
Azar et al.

(10) Patent No.: US 11,357,619 B2
(45) Date of Patent: Jun. 14, 2022

(54) ADJUSTABLE OPHTHALMIC DEVICES, SYSTEMS, AND METHODS OF ADJUSTMENT

(71) Applicant: Verily Life Sciences LLC, South San Francisco, CA (US)

(72) Inventors: Dimitri Azar, San Francisco, CA (US); Stein Kuiper, South San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 140 days.

(21) Appl. No.: 16/664,726

(22) Filed: Oct. 25, 2019

(65) Prior Publication Data

US 2020/0129288 A1 Apr. 30, 2020

Related U.S. Application Data

(60) Provisional application No. 62/753,616, filed on Oct. 31, 2018.

(51) Int. Cl.
*A61F 2/16* (2006.01)
*A61F 9/008* (2006.01)

(52) U.S. Cl.
CPC .......... *A61F 2/1648* (2013.01); *A61F 2/1627* (2013.01); *A61F 9/00812* (2013.01);
(Continued)

(58) Field of Classification Search
CPC .... A61F 2/1648; A61F 2/1627; A61F 2/1635; A61F 2/1624; A61F 9/00812;
(Continued)

(56) References Cited

U.S. PATENT DOCUMENTS 7,438,723 B2 * 10/2008 Esch .................... A61F 2/1635
623/6.13
8,579,971 B2 11/2013 Webb
(Continued)

OTHER PUBLICATIONS

Keenan, Joseph, "FDA clears RxSight's light-adjustable Intraocular lens for implants," FierceBiotech, retrieved Mar. 28, 2018, from URL https://www.fiercebiotech.com/medtech/fda-clears-rxsight-s-light-adjustable-irttraocular-leris-for-implants.
(Continued)

*Primary Examiner* — Paul B Prebilic
(74) *Attorney, Agent, or Firm* — Christensen O'Connor Johnson Kindness PLLC

(57) ABSTRACT

Adjustable ophthalmic devices, systems including adjustable ophthalmic devices, and methods of adjusting an optical power of an ophthalmic device are described. In an embodiment, the ophthalmic devices include a body including an inner surface defining an aperture through the body, wherein the inner surface includes a feature selected from a sharp surface feature, a layer on at least a portion of the inner surface having a surface energy different than a surface energy of the inner surface, and a combination thereof. In an embodiment, the ophthalmic device includes two immiscible liquids disposed in the aperture defining a meniscus, wherein a curvature of the meniscus is defined at least in part by a position of an interface between the layer and the inner surface, a position of the sharp surface feature, or combination thereof.

8 Claims, 7 Drawing Sheets

(52) U.S. Cl.
CPC ............... *A61F 2009/00887* (2013.01); *A61F 2220/0016* (2013.01)

(58) Field of Classification Search
CPC ........ A61F 9/00814; A61F 2009/00887; A61F 2220/0016; A61F 2230/0065; A61F 2250/0004; A61F 2250/0009; A61F 2250/0013; A61F 2250/0053; A61F 2250/0056; A61F 2250/0091
See application file for complete search history.

(56) References Cited

U.S. PATENT DOCUMENTS

| | | |
|---|---|---|
| 9,016,860 B2 | 4/2015 | Peyman |
| 2009/0264998 A1 | 10/2009 | Mentak et al. |
| 2011/0196487 A1* | 8/2011 | Badawi ................. A61F 9/0017 623/4.1 |
| 2012/0057244 A1 | 3/2012 | Pugh et al. |
| 2012/0059363 A1* | 3/2012 | Bor ....................... A61F 9/0017 606/5 |
| 2015/0105760 A1 | 4/2015 | Rao et al. |
| 2016/0296662 A1 | 10/2016 | Stoy et al. |

OTHER PUBLICATIONS

International Search Report and Written Opinion dated Feb. 12, 2020 for corresponding International Patent Application No. PCT/US2019/058511, 12 pages.

* cited by examiner

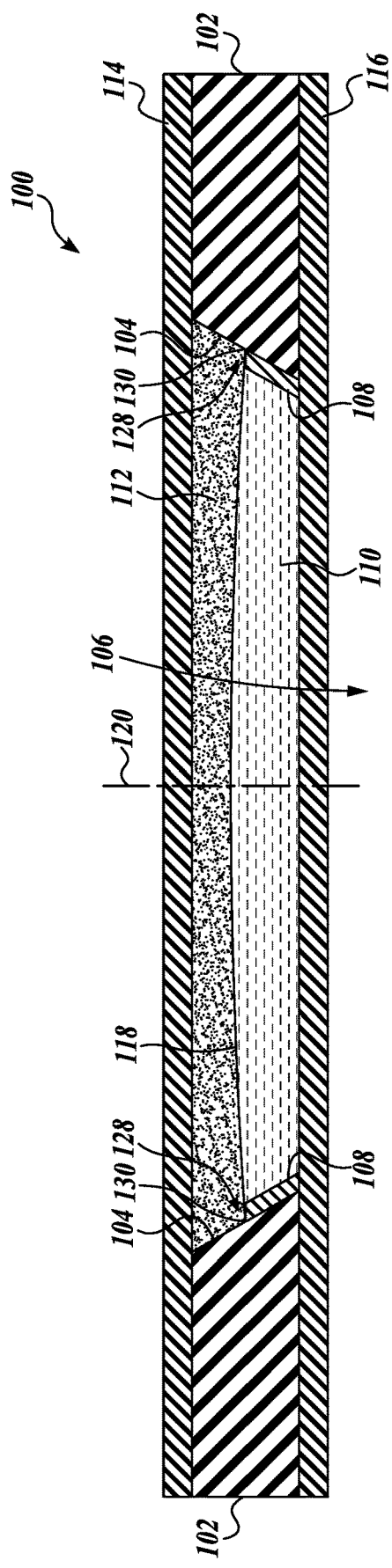
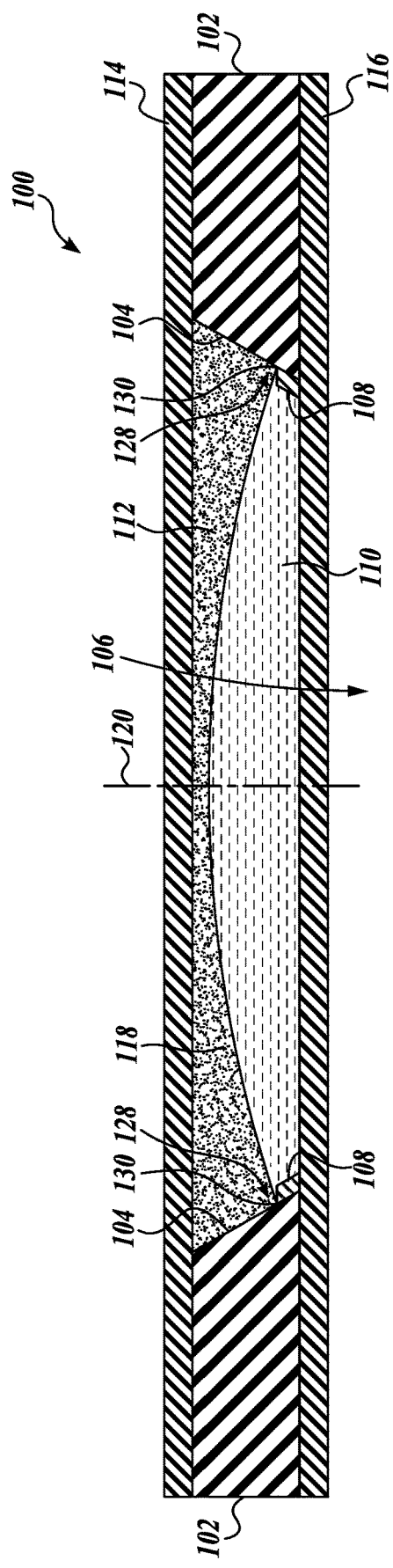
FIG. 1A
FIG. 1B

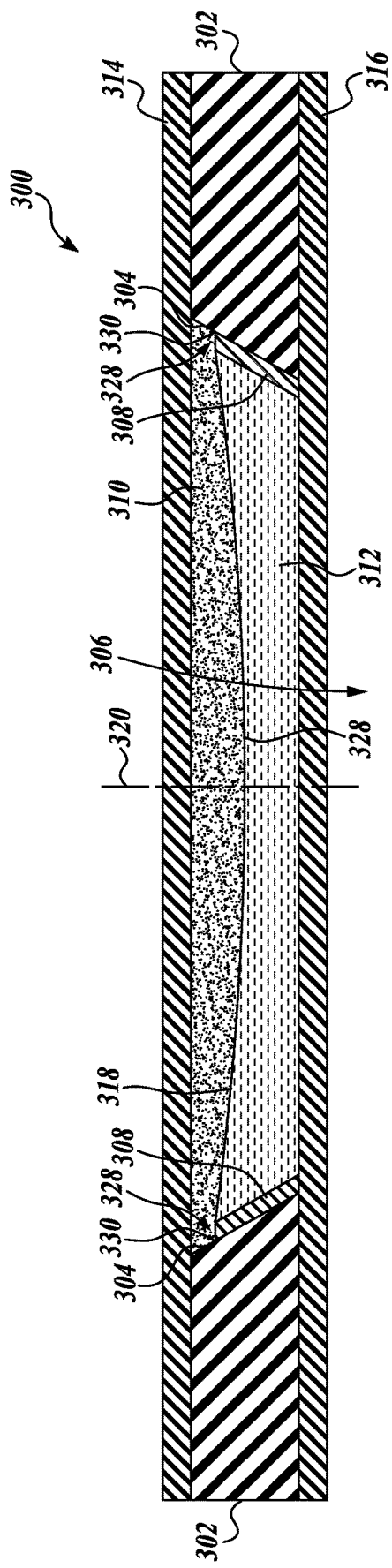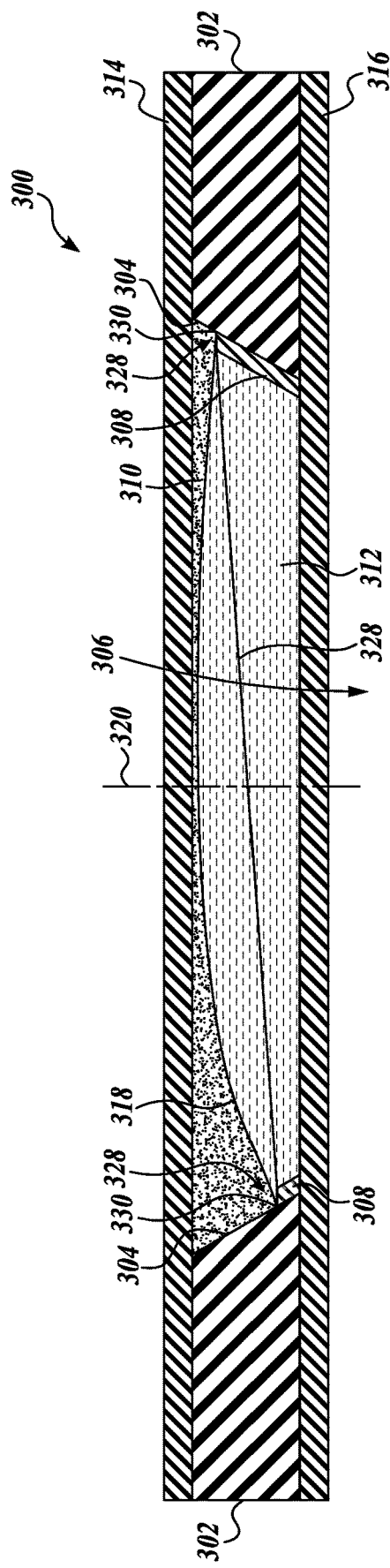

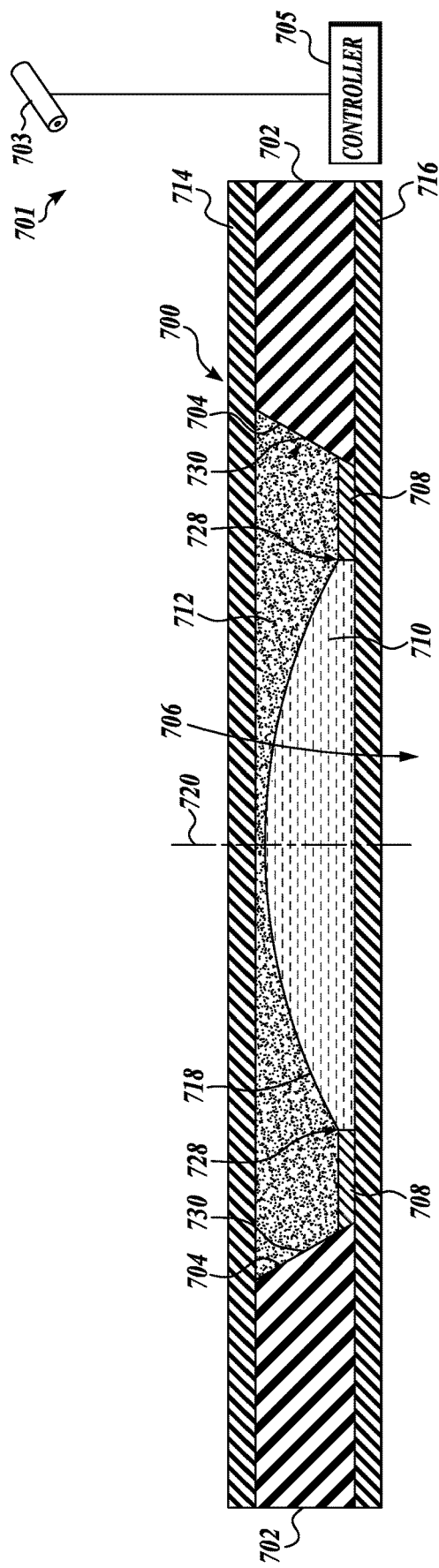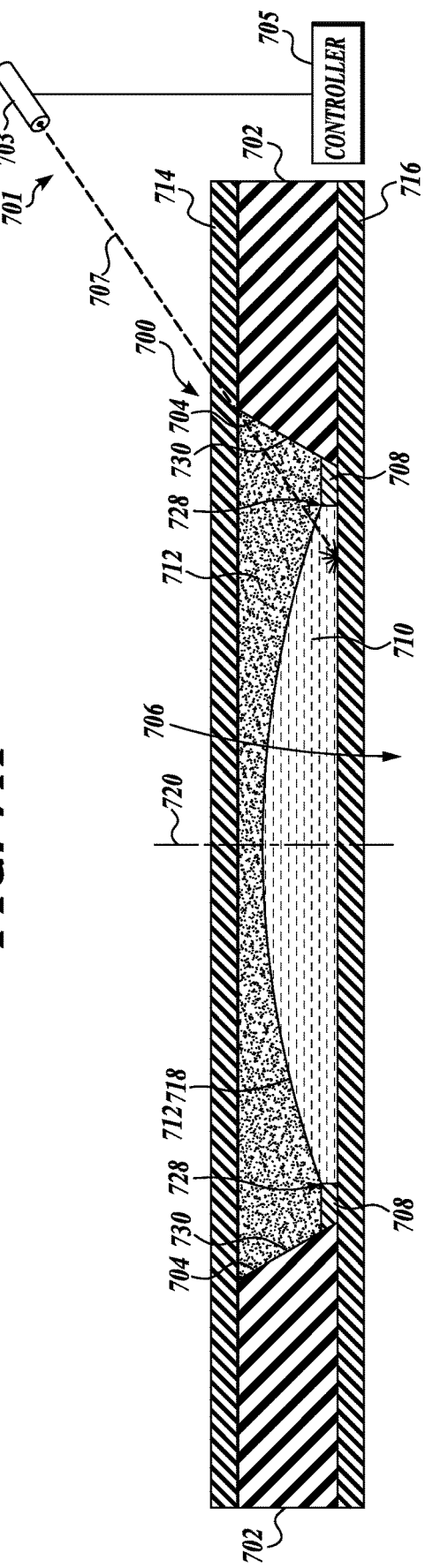

ADJUSTABLE OPHTHALMIC DEVICES, SYSTEMS, AND METHODS OF ADJUSTMENT

CROSS-REFERENCE TO RELATED APPLICATION

This application claims the benefit of U.S. Provisional Application No. 62/753,616, filed Oct. 31, 2018, which is hereby incorporated by reference in its entirety.

TECHNICAL FIELD

This disclosure relates generally to ophthalmic devices, and, in particular but not exclusively, relates to intraocular lenses.

BACKGROUND INFORMATION

In treatment of, for example, cataracts, an ophthalmic device, such as an intraocular lens, is implanted into an eye of a patient. After implantation of the ophthalmic device, the patient often still needs some additional optical correction in the form of, for example, spectacles, contact lenses, or laser surgery because the eye including the ophthalmic device does not have a predicted or desired optical power. It is thought that a common reason for such a refractive surprise is a position where the intraocular lens settles within the eye. For some patients, especially those with irregular corneas or those who have previously undergone laser-assisted in situ keratomileusis (LASIK) procedures, the refractive surprise can be as high as, for example, 3-5 diopters. There may also be associated unexpected astigmatism, as well, often amounting to fewer than 0.75 diopters.

BRIEF DESCRIPTION OF THE DRAWINGS

Non-limiting and non-exhaustive embodiments of the claimed subject matter are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIG. 1A is a cross sectional view of an ophthalmic device, in accordance with an embodiment of the disclosure.

FIG. 1B is another cross sectional view of the ophthalmic device of FIG. 1A, in accordance with an embodiment of the disclosure.

FIG. 3A is a cross sectional view of an ophthalmic device, in accordance with an embodiment of the disclosure.

FIG. 3B is another cross sectional view of the ophthalmic device of FIG. 3A, in accordance with an embodiment of the disclosure.

FIG. 7A illustrates a system including an ophthalmic device, in accordance with an embodiment of the disclosure.

FIG. 7B illustrates another view of the system of FIG. 7A, in accordance with an embodiment of the disclosure.

DETAILED DESCRIPTION

Figure 2A:
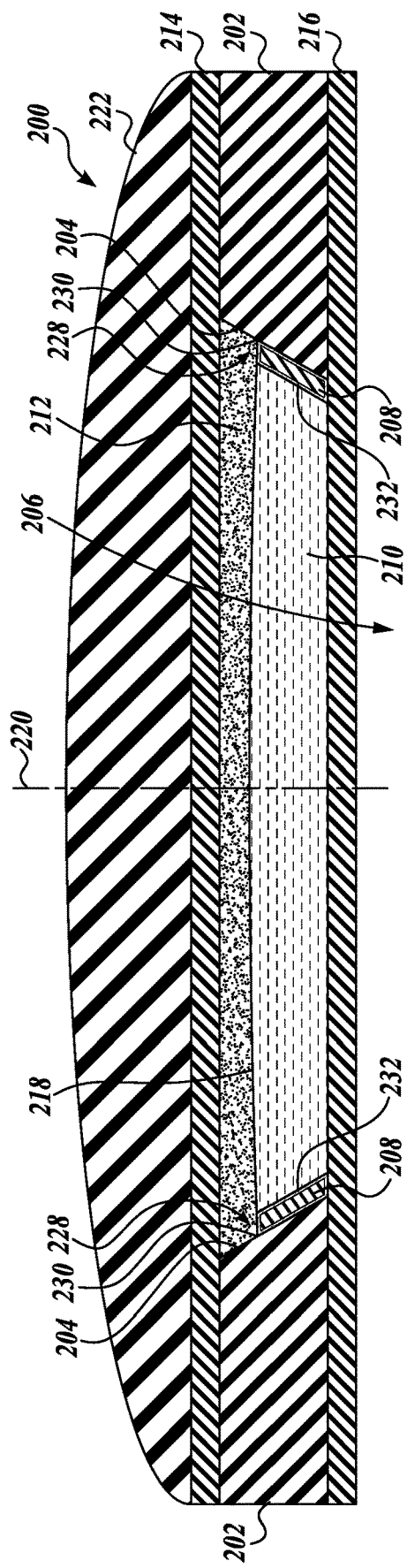
FIG. 2A is a cross sectional view of an ophthalmic device, in accordance with an embodiment of the disclosure.

Embodiments of an ophthalmic device, a system, and a method for adjusting an optical power of the ophthalmic device are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

FIGS. 1A and 1B are cross sectional views of an ophthalmic device 100, in accordance with an embodiment of the disclosure. Ophthalmic device 100 is shown to include an annular body 102 including an inner surface 104 defining an aperture 106 through annular body 102, a layer 108 disposed on a portion of the inner surface 104, a first liquid 110 and a second liquid 112 disposed in aperture 106, and first optical window 114 and second optical window 116 coupled to opposite sides of annular body 102. As discussed further herein, the ophthalmic device 100 has a base optical power, and wherein the layer 108 is reconfigurable to adjust the base optical power.

Annular body 102, as well as other annular bodies described herein, is generally annulus shaped (see, e.g. annular body 402) having a generally toroidal form. While annular bodies being annulus shaped are described herein, other embodiments provide bodies having shapes other than annuli. For example, in certain embodiments according to the present disclosure, the ophthalmic device 100 includes bodies having a shape suitable for forming an ophthalmic device other than an annulus. Such shapes can include, without limitation, a disc, a lens, a regular polygon, an irregular polygon, a free shape, and the like. In an embodiment, the bodies of the present disclosure include bodies having a rectangular outer edge and a circular inner surface defining a circular aperture.

In an embodiment, inner surface 104 is cylindrical. The inner surface 104 may have a conical frustum shape such that the inner surface 104 is at an acute or otherwise non-parallel angle to the optical axis 120 of the ophthalmic device 100. In some embodiments, the inner surface 104 is at 45° relative to the optical axis 120.

The ophthalmic devices described herein, such as ophthalmic device 100, include intraocular lenses for insertion into an eye, such as during treatment of, e.g., cataracts or myopia. However, while intraocular lenses are discussed further herein, it will be understood that the ophthalmic devices of the present disclosure include, for example, contact lenses to be worn on an outside surface of any eye and other ophthalmic devices.

Referring still to FIGS. 1A and 1B, first liquid 110 and second liquid 112 are immiscible and define a meniscus 118. The first liquid 110 and second liquid 112 can be any optically clear or transmissive, immiscible liquids configured to define a meniscus when disposed together in an aperture, such as aperture 106. In an embodiment, the first liquid 110 is an aqueous solution, such as a saline solution, and the second liquid 112 is an oil, such as a silicone oil. As discussed further herein, an optical power of the ophthalmic device 100 is defined at least in part by a difference in refractive indices of the first liquid 110 and the second liquid 112 and on a curvature of the meniscus 118.

As shown, the layer 108 is wet by the first liquid 110 and is not or substantially not wet by the second liquid 112. Likewise, the inner surface 104 is wet by the second liquid 112 and is not or substantially not wet by the first liquid 110. In this regard, a curvature of meniscus 118 is defined at least in part by an interface 128 of layer 108 and an exposed portion of inner surface 104 at which meniscus 118 is pinned. As shown, layer 108 coats at least a portion of inner surface 104. As discussed further herein, by adjusting a position of the interface 128 between layer 108 and inner surface 104, the curvature of meniscus 118 is correspondingly adjusted.

In an embodiment, layer 108 has a surface energy different than a surface energy of inner surface 104. For example, in an embodiment, the layer 108 is hydrophobic such that, for example, it causes a polar liquid disposed in aperture 106 to de-wet and a meniscus 118 defined by the first liquid 110 and second liquid 112 to form a convex or concave shape having an optical power. In an embodiment, the hydrophobic layer 108 includes a hydrophobic layer material selected from the group consisting of an amorphous fluorocarbon, an amorphous hydrocarbon, a hydrophobic silane, and combinations thereof. In an embodiment, the layer 108 includes trimethoxyperfluorodecane. In an embodiment, the layer 108 is slightly polar and the first liquid 110 is also slightly polar while still immiscible with the second liquid 112. In an embodiment, the slightly polar layer 108 includes a material selected from the group consisting of parylene-C, polyimide, polyetherimide, and combinations thereof. In an embodiment, layer 108 includes a heat-shrink material, as discussed further herein with respect to FIGS. 7A and 7B. In an embodiment, the slightly polar first liquid 110 is a phenylated silicon oil. In an embodiment, the inner surface 104 is hydrophilic. In an embodiment, the hydrophilic inner surface 104 includes a hydrophilic inner surface material selected from the group consisting of silicon dioxide, gold, polyethylene glycol (PEG), polyacrylic acid, hydrophilic silane (such as hydroxyalkyl-terminated silane), and combinations thereof. In an embodiment, the inner surface 104 of the annular body 102 includes a layer (not shown) facing aperture 106 and interfacing with layer 108 disposed over a bulk material of the annular body 102. In another embodiment, inner surface 104 comprises material including the bulk material annular body 102.

Alternatively, in an embodiment, the layer 108 is hydrophilic and inner surface 104 is hydrophobic. In an embodiment, the layer 108 includes PEG and the inner surface 104 includes a hydrophobic hydrocarbon. In an embodiment, the hydrophilic layer 108 includes a hydrophilic layer material selected from the group consisting of gold, PEG, polyacrylic acid, hydroxyalkyl-terminated silane, and combinations thereof. In an embodiment, the hydrophobic inner surface includes a hydrophobic inner surface 104 material selected from the group consisting of an amorphous fluorocarbon, an amorphous hydrocarbon, a hydrophobic silane, and combinations thereof.

In an embodiment, the inner surface 104 includes silica and the layer 108 includes a fluorosilane.

The ophthalmic device 100 is shown to include an interface 128 between layer 108 and inner surface 104. In the illustrated embodiment, the interface 128 includes vertex 130. As above, a meniscus, such as meniscus 118, can be pinned to a portion of inner surface 104 due a difference in surface energies between the layer 108 and inner surface 104. However, a meniscus, such as meniscus 118, can be pinned to inner surface 104 by a change in surface geometry, such as a sharp surface feature or corner, illustrated here as vertex 130. While the change in surface geometry is illustrated as a vertex 130 defined at least in part by layer 108 and inner surface 104, a change in geometry can include, for example, a high-aspect-ratio or sharp feature of inner surface 104 configured to pin meniscus 118 in the absence of a layer, such as layer 108, disposed on inner surface 104. Likewise, in an embodiment, the sharp surface feature includes a ring protruding from a portion of the inner surface 104 having a generally acute cross sectional angle (not shown). Additionally, in an embodiment, the sharp surface feature, such as vertex 130, pins meniscus 118 to inner surface 104 without a difference in surface energies between layer 108 and inner surface 104. As discussed further herein, by ablating or otherwise removing all or a portion of layer 108 or otherwise changing a position of the sharp surface feature, a curvature of meniscus 118 and an optical power of ophthalmic device 100 are changed.

In an embodiment, the layer 108 is applied to the inner surface 104 through coating the inner surface 104 with the layer 108, such as by spraying, depositing, evaporation, dip coating, and the like. In an embodiment, the layer 108 is adhered or otherwise attached to the inner surface 104, such as with an adhesive or a fastener (not shown). In an embodiment, the layer 108 includes a silane with a hydrophobic tail terminating with a hydrophilic group that is cleaved upon illumination with laser light.

In an embodiment, the layer 108 is configured to ablate. In an embodiment, the layer 108 is configured to ablate upon illumination with laser light, such as from a femto-second laser used in a LASIK procedure. As used herein, "ablation" refers to removal of material, such as a portion of a layer, from the surface of an object, such as an inner surface of an annular body, by vaporization, chipping, or other erosive processes.

Layer 108 has a thickness. In an embodiment, layer 108 is disposed on inner surface 104 as an atomic monolayer. In certain other embodiments, layer 108 has thickness greater than a monolayer having thickness of, e.g., between several atomic layers and several micrometers. As discussed further herein, a curvature of meniscus 118 is defined at least in part by a thickness of layer 108.

As discussed further herein, the ophthalmic device 100 has a base optical power, and wherein the layer 108 is reconfigurable to adjust the base optical power. In this regard, the base optical power is adjustable in situ, such as implanted in an eye, to correct for a refractive surprise after implantation. FIG. 1A shows ophthalmic device 100 in a first state including layer 108 having a first height. FIG. 1B shows ophthalmic device 100 in a second state including layer 108 having a second height less than the first height. As discussed further herein, adjusting a height, thickness, shape, or position of a layer, such as layer 108, may be accomplished in a number of ways including by laser ablation.

As shown in FIGS. 1A and 1B, by lowering a height of layer 108 relative to, for example, second optical window 116, the interface 128 between layer 108 and inner surface 104 is lowered, thereby altering the curvature of meniscus 118. With a lower layer height and, accordingly a lower interface 128 between layer 108 and inner surface 104, meniscus 118 has a larger curvature and, accordingly, an optical power of ophthalmic device 100 is altered.

As discussed above, curvature of the meniscus 118 is defined at least in part by a position of an interface 128 between the layer 108 and the inner surface 104. The curvature of the meniscus 118 may be further defined by at least one of a shape of the annular body 102, a shape of interface 128 between the layer 108 and the inner surface 104, and relative volumes of the first liquid 110 and second liquid 112 disposed in aperture 106.

As shown, annular body 102 is symmetric about optical axis 120. In the illustrated embodiment, the height of layer 108 has been altered rotationally symmetrically with respect to optical axis 120 of ophthalmic device 100. In embodiment, a height of the layer is even with respect to optical axis 120. In this regard, ophthalmic device 100 is configured to correct for, e.g., myopia and hyperopia.

In an embodiment, the layer 108 is a first layer and the ophthalmic device 100 further includes a second layer (not shown) disposed on the first layer 108. Further, in an embodiment, the second layer has a surface energy that is different than the surface energy of the first layer 108 and that is equal to or substantially equal to the surface energy of the inner surface 104. In an embodiment, the ophthalmic device 100 includes a plurality of layers disposed on inner surface 104 that alternate between, for example, hydrophilic layers and hydrophobic layers.

Figure 2B:
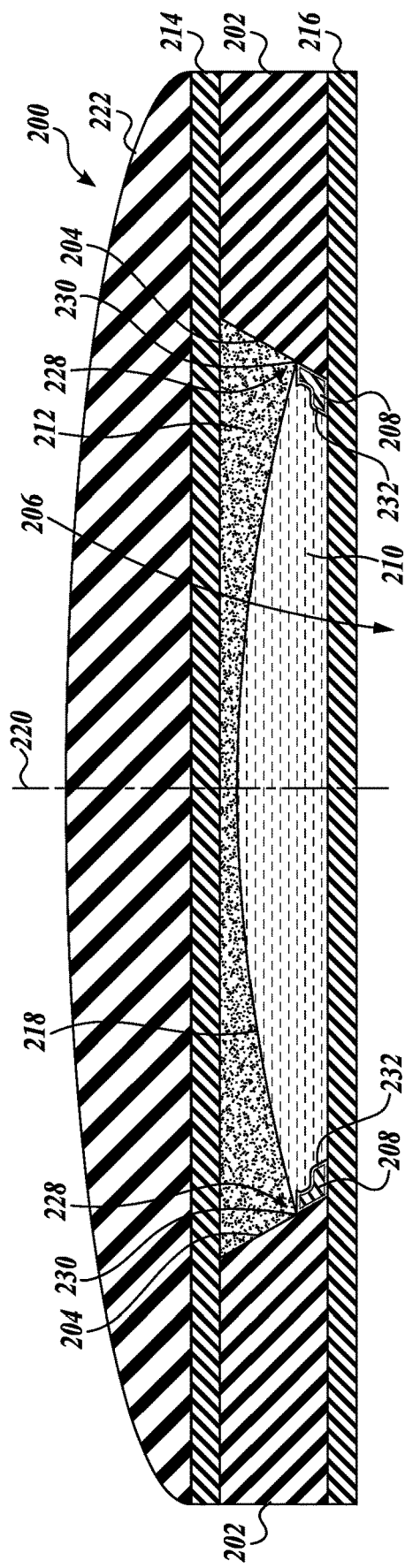
FIG. 2B is another cross sectional view of the ophthalmic device of FIG. 2A, in accordance with an embodiment of the disclosure.

In an embodiment, the ophthalmic devices of the present disclosure include a layer that includes a phase-change material. In that regard, attention is directed to FIGS. 2A and 2B in which an ophthalmic device 200 according to an embodiment of the present disclosure is illustrated. FIGS. 2A and 2B are cross sectional views of an ophthalmic device 200. Ophthalmic device 200 is shown to include an annular body 202 including an inner surface 204 defining an aperture 206 through annular body 202, a layer 208 including a phase-change material disposed on a portion of the inner surface 204, first liquid 210 and second liquid 212 immiscible with first liquid 210 disposed in aperture 206, and first optical window 214 and second optical window 216 coupled to opposite sides of annular body 202. Ophthalmic device 200 is shown to be symmetric about optical axis 220. In an embodiment, ophthalmic device 200 is an example of ophthalmic device 100.

In an embodiment, the phase-change material is a solid-liquid phase-change material, configured to transition from a solid to a liquid upon exposure to an energy source, such as a light source or a heat source. In an embodiment, the phase-change material is a wax, such as a paraffin wax or bees wax.

FIG. 2A illustrates ophthalmic device 200 in a first state, such as before exposure to an energy source. In the illustrated embodiment, layer 208 coats a portion of inner surface 204 and is shaped to expose a portion of the inner surface 204 upon transitioning from a first phase to a second phase. FIG. 2B illustrates ophthalmic device 200 in a second state after layer 208 including the phase-change material has been exposed to an energy source and has transitioned from a first phase to a second phase. In this regard, a larger portion of inner surface 204 has been exposed to the first liquid 210 and the second liquid 212. Furthermore, interface 228 has moved from a first height as illustrated in FIG. 2A to a second lower height as shown in FIG. 2B, thus changing a curvature of meniscus 218 and an optical power of ophthalmic device 200. As discussed further herein, layer 208 of ophthalmic device 200 is configured to be altered in situ to correct for a refractive surprise after implantation.

In the illustrated embodiment, layer 208 including the phase-change material is covered or otherwise encapsulated by an elastomeric layer 232. Elastomeric layer 232 is elastomeric and, due to its viscoelasticity, facilitates layer 208 assuming the second lower height as shown in FIG. 2B when the phase-change material of layer 208 changes phases. In that regard, when the phase-change material changes phase, the layer 208 changes shape under the influence of built-in stress of the elastomeric layer 232. Elastomeric layer 232 further prevents or reduces interactions between layer 208 and first liquid 210 and second liquid 212. In another embodiment (not shown), ophthalmic device 200 does not include elastomeric layer 232 and layer 208 is exposed to first liquid 210 and second liquid 212. In this regard, the phase-change material of layer 208 assumes the second height shown in FIG. 2B when the phase-change material changes phases due in part to interfacial tension between the phase-change material of layer 208 and first liquid 210 and second liquid 212.

Ophthalmic device 200 is illustrated to further include a base lens 222 coupled to annular body 202. Base lens 222 has a static optical power, whereas an optical power of other portions of ophthalmic device including, for example, annular body 202, layer 208, inner surface 204, first liquid 210, and second liquid 212, are adjustable, as discussed further herein. In an embodiment, base lens 222 has an optical power configured to provide a majority of a needed optical correction and other portions of ophthalmic device 200 are configured to provide a remaining portion of the needed optical correction. Additionally, as described further herein, portions of ophthalmic device 200 including, inter alia, layer 208 and inner surface 204 are configured to adjust an optical power of ophthalmic device 200 and an eye including ophthalmic device 200 implanted therein.

In this regard, a combination of a base lens 220 with a fixed optical power and tunable components of ophthalmic device 200 are employed to correct the total refractive error of the post-operative eye. In an embodiment, the base lens 222 has, e.g., 90% or more of the total optical power of the ophthalmic device 200 and tunable portions of ophthalmic device 200 (such as layer 208, inner layer 204, meniscus 218, etc.) are configured to provide the remaining optical power. If there is a need to tune the ophthalmic device 200 after, for example, implantation into an eye, laser energy may be used to alter the curvature of the meniscus 218 without affecting the base lens 222. In the case of high preoperative astigmatism, an astigmatic (toric) base lens could be used to correct 90% or more of the astigmatism. Residual or surgically induced post-operative astigmatism/myopia/hyperopia can be corrected by applying, for example, laser pulses to the tunable portions of ophthalmic device 200 to adjust the optical power of such tunable portions, as discussed further herein.

In the illustrated embodiment, base lens 222 is shown coupled to first optical window 214. However, in an embodiment, one or more of the first optical window 214 and the second optical window 216 each have a static optical power, such as by having a curved form configured refract incident light.

FIGS. 3A and 3B are cross sectional views of an ophthalmic device 300, in accordance with an embodiment of the disclosure. Ophthalmic device 300 is shown to include an annular body 302 including an inner surface 304 defining an aperture 306 through annular body 302, a layer 308 disposed on a portion of the inner surface 304, first liquid 310 and second liquid 312 disposed in aperture 306, and first optical window 314 and second optical window 316 coupled to opposite sides of annular body 302. In an embodiment, ophthalmic device 300 is an example of ophthalmic devices 100 and 200.

In the illustrated embodiment, annular body 302 is symmetric about optical axis 320. FIG. 3A illustrates ophthalmic device 300 in a first state, such as before altering a portion of layer 308, wherein layer 308 has a height that is rotationally symmetric with respect to optical axis 320. FIG. 3B illustrates ophthalmic device 300 in a second state, such as after altering a portion of layer 308, wherein layer 308 has a height that rotationally asymmetric with respect to optical axis 320. In this regard, one portion of layer 308 has a height that is larger than another portion of layer 308. Interface 328 is shown in FIG. 3B to have a cross section that is non-orthogonal to optical axis 320. Accordingly, meniscus 318 is shown to have a curvature that is symmetric with respect to optical axis 320 in FIG. 3A, whereas meniscus 318 is shown to have a curvature that is asymmetric with respect to optical axis 320 in FIG. 3B. As discussed further herein with respect to method 500, circularly asymmetric alteration of layer 308 and meniscus 318 can be used to make corrections for astigmatisms, such as myopic astigmatism, hyperopic astigmatism, mixed astigmatism, and the like.

As shown in FIGS. 3A and 3B, asymmetric alteration of layer 308 is accomplished through ablation. However, asymmetric alteration of layer 308 can be accomplished by any of the methods described herein, such as, for example, by phase transition of a phase-change material, chemical modification of a chemically modifiable material, and changing a charge retention property of a charge-retaining material.

Figure 4:
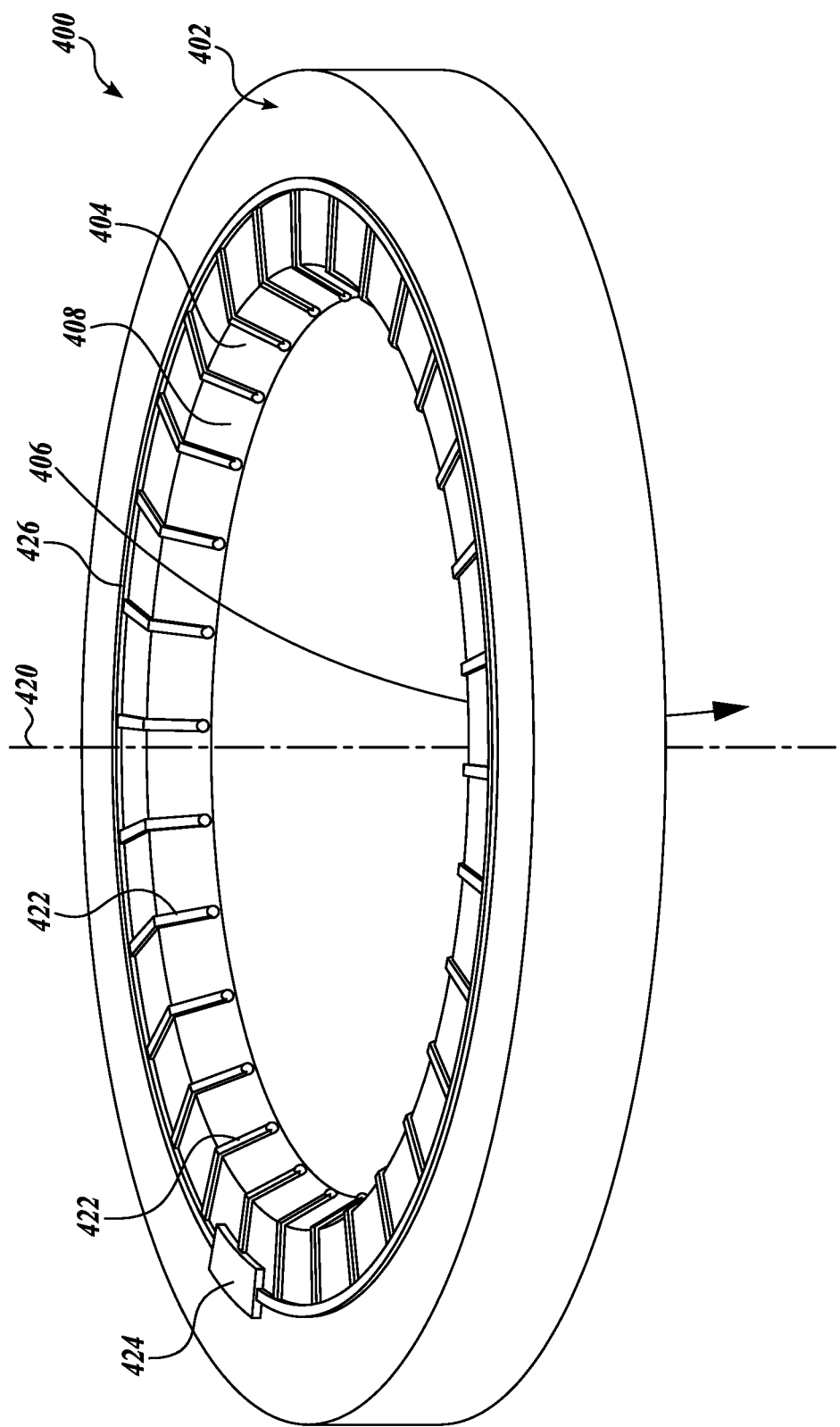
FIG. 4 is a perspective view of an ophthalmic device, in accordance with an embodiment of the disclosure.

FIG. 4 is a perspective view of an ophthalmic device 400, in accordance with an embodiment of the disclosure. As illustrated, ophthalmic device 400 includes an annular body 402 including an inner surface 404 defining an aperture 406, a layer 408 disposed on a portion of inner surface 404, a plurality of circuits 422 embedded in layer 408, and a controller 424 operably coupled to the plurality of circuits 422 through connector 426. In an embodiment, each of the plurality of circuits 422 includes a fuse (not shown) configured to melt or otherwise burn out and ablate or otherwise remove a portion of layer 408 adjacent to the fuse when a voltage is applied. Annular body 402 is shown to be rotationally symmetric about optical axis 420.

In an embodiment, controller 424 includes logic that when executed by the controller 424 causes the ophthalmic device 400 to perform operations including applying a voltage to one or more of the plurality of circuits 422 sufficient to ablate a portion of the layer 408 adjacent to the one or more of the plurality of circuits 422.

As shown, ophthalmic device 400 includes aperture 406 shaped to receive, e.g., a first liquid and a second liquid immiscible with the first liquid. In an embodiment, ophthalmic device 400 further includes a first liquid and a second liquid immiscible with the first liquid disposed in aperture 406 (not shown, see e.g. FIGS. 1A, 1B, 2A, 2B, 3A, and 3B). As discussed further herein with respect to FIGS. 1A, 1B, 2A, 2B, 3A, and 3B, such immiscible liquids disposed in apertures of annular bodies form meniscuses configured to refract incident light and have an optical power. By applying a voltage to one or more of the plurality of circuits 422 and ablating a portion of the layer 408 adjacent to the one or more of the plurality of circuits 408, a curvature of a meniscus defined by the first liquid and the second liquid and optical power of ophthalmic device 400 are correspondingly adjusted.

In an embodiment, the operations include applying a voltage to one or more of the plurality of circuits 422 that are rotationally symmetric with respect to an optical axis 420 of the ophthalmic device 400. As discussed further herein with respect to FIGS. 1A and 1B, such symmetric ablation and corresponding adjustment of optical power is useful in correcting, for example, myopia and hyperopia.

In an embodiment, the operations include applying a voltage to one or more of the plurality of circuits 422 that are rotationally asymmetric with respect to an optical axis 420 of the ophthalmic device 400. In this regard, a rotationally asymmetric portion of the layer 408 adjacent to the plurality of circuits is ablated. As discussed further herein with respect to FIGS. 3A and 3B, such asymmetric ablation and corresponding adjustment of optical power is useful in correcting, for example, various astigmatisms or other optical aberrations.

In an embodiment, the ophthalmic device 400 is configured to provide power to the plurality of circuits 422 in situ, such as implanted in an eye.

FIGS. 7A and 7B illustrate a system 701 in accordance with an embodiment of the disclosure. System 701 includes an ophthalmic device 700, a laser 703, and a controller 705 operably coupled to laser 703.

As illustrated, ophthalmic device 700 includes an annular body 702 including an inner surface 704 defining an aperture 706, first optical window 714 and second optical window 716 coupled to opposite sides of annular body 702, a layer 708 disposed on second optical window 716, first liquid 710 and second liquid 712 disposed in aperture 706. Ophthalmic device 700 is symmetric about optical axis 720. In an embodiment, ophthalmic device 700 is an example of ophthalmic devices 100, 200, 300, and 400.

Controller 705 includes logic that when executed by controller 705 causes the controller to perform certain operations. These operations can include illuminating a portion of the layer 708. In an embodiment, the operations include illuminating a portion of the layer 708 sufficient to ablate the illuminated portion of the layer 708. In an embodiment the layer 708 includes material configured to decrease in volume upon illumination with laser light. Such material can include, for example, a foam configured to transform into a denser material having no or fewer pores than the foam. In an embodiment, the material configured to decrease in volume upon illumination with laser light includes a heat-shrink material configured to decrease in volume when exposed to heat. In an embodiment, the layer 708 includes material configured to increase in volume upon illumination with laser light (not shown), such as a solid material configured to foam upon illumination with laser light. As shown in FIGS. 7A and 7B, ophthalmic device includes layer 708 disposed on at least a portion of second optical window 716. In an embodiment, the operations include illuminating the portion of layer 708 disposed on the second optical window 716, such as with laser light 707. Such illumination can also or alternatively include illumination with light sources other than laser light 707 of a wavelength and having a sufficient intensity to ablate or otherwise remove layer 708 from second optical window 716. In an embodiment, the operations include illuminating a portion of layer 708 disposed on the inner surface 704 of annular body 702 (not shown). In an embodiment, layer 708 is not in contact with inner surface 704 of annular body 702, such as when an intervening layer (not shown) is disposed between layer 708 and inner surface 704.

FIG. 7A illustrates ophthalmic device 700 including layer 708, such as a foam or a heat-shrink material, in a first state prior to illumination with laser 703 and having a first length. FIG. 7B illustrates ophthalmic device 700 during illumination showing the portion of layer 708, now in a second state such as a solid polymer, disposed on a portion of second optical window 716 and having a second length less than the first length. In that regard, a length of the layer 708 is decreased and a curvature of meniscus 718 is altered, thereby altering an optical power of ophthalmic device 701. In addition to a length of layer 708 disposed on second optical window 716, the curvature of meniscus 718 is defined in part by interface 728 to which meniscus 718 is pinned at or adjacent to a periphery of aperture 706.

As discussed further herein with respect to method 500, in an embodiment, ophthalmic device 700 is implanted in an eye of a patient and laser 703 is disposed outside of the eye when layer 708 is illuminated. In this regard, an optical power of ophthalmic device 700 is configured to be altered in situ, such as after an implantation of the ophthalmic device into an eye.

Figure 6:
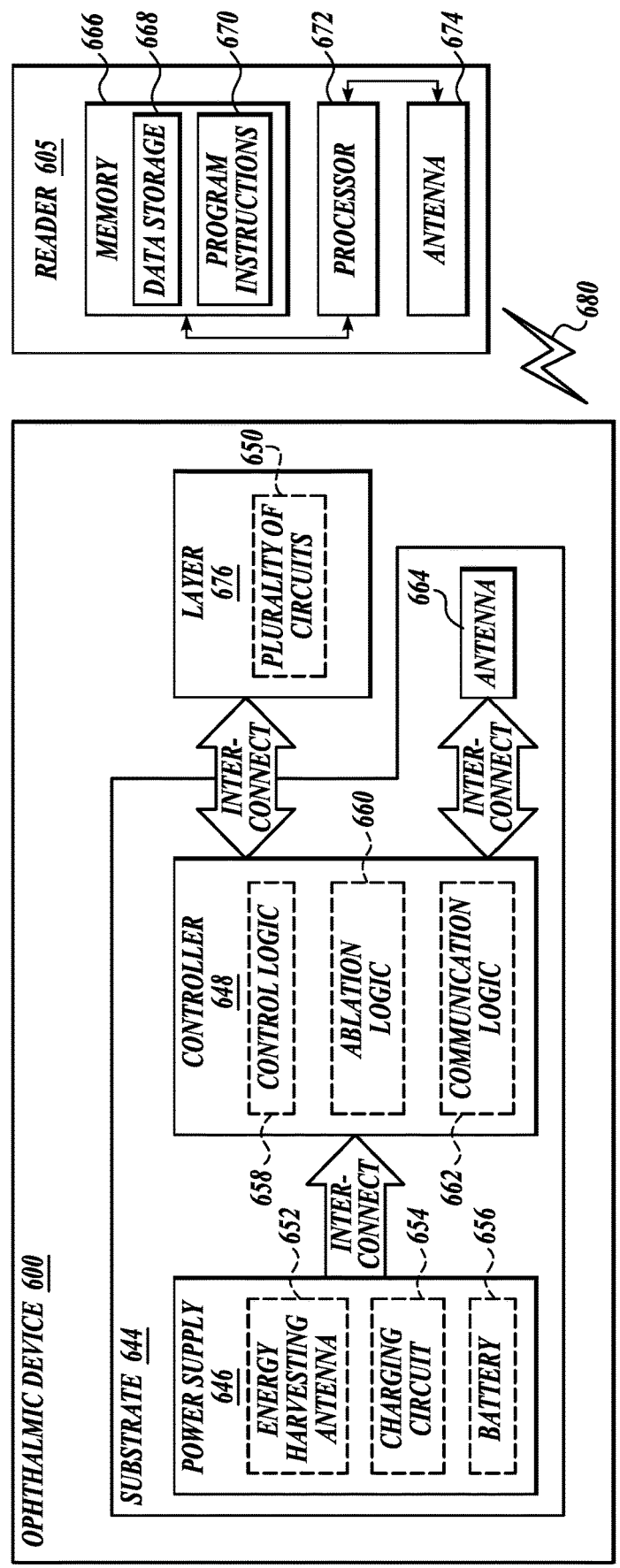
FIG. 6 is a functional block diagram of an ophthalmic device including a layer disposed on an annular body, in accordance with an embodiment of the present disclosure.

FIG. 6 is a functional block diagram of an ophthalmic device 600 including a layer disposed on an annular body, in accordance with an embodiment of the present disclosure. Ophthalmic device 600 may be an implantable device, such as an intraocular lens. In an embodiment, ophthalmic device 600 is an example of ophthalmic devices 100, 200, 300, 400, and 700. In the depicted embodiment, ophthalmic device 600 includes a substrate 644 configured to be implanted into an eye. The substrate 644 is configured to provide a mounting surface for a power supply 646, a controller 648, an antenna 664, and various interconnects. The substrate 644 and the associated electronics may be one implementation of the controller 424 and an associated annular body, such as the annular body 402. The illustrated embodiment of power supply 646 includes an energy harvesting antenna 652, charging circuitry 654, and a battery 656. The illustrated embodiment of controller 648 includes control logic 658, ablation logic 660, and communication logic 662. In an embodiment, ablation logic 660 is optional and can be supplied by an external device, such as reader 605.

Power supply 646 supplies operating voltages to the controller 648 and/or the plurality of circuits 650. Antenna 664 is operated by the controller 648 to communicate information to and/or from ophthalmic device 600. In the illustrated embodiment, antenna 664, controller 648, and power supply 646 are disposed on/in substrate 644. In one embodiment, plurality of circuits 650 is disposed on an inner surface of the substrate 644, such as the inner surface 404 of annular body 402, and is embedded in a layer, such as layer 408.

Substrate 644 includes one or more surfaces suitable for mounting controller 648, power supply 646, and antenna 664. Substrate 644 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on substrate 644 to form circuitry, electrodes, etc. For example, antenna 664 can be formed by depositing a pattern of gold or another conductive material on substrate 644. Similarly, interconnects can be formed by depositing suitable patterns of conductive materials on substrate 644. A combination of resists, masks, and deposition techniques can be employed to pattern materials on substrate 644. Substrate 644 can be a relatively soft material, such as a polymer or another material sufficient to structurally support the circuitry and/or electronics while being flexible enough to be rolled or folded. Ophthalmic device 600 can alternatively be arranged with a group of unconnected substrates rather than a single substrate 644. For example, controller 648 and power supply 646 can be mounted to one substrate 644, while antenna 664 is mounted to another substrate and the two can be electrically connected via interconnects.

Substrate 644 can be shaped as a flattened ring with a radial width dimension sufficient to provide a mounting platform for the embedded electronic components. Substrate 644 can have a thickness sufficiently large to provide structural stability suitable for supporting the electronics mounted thereon. For example, substrate 644 can be shaped as a ring with a diameter of about 10 millimeters, a radial width of about 1 millimeter (e.g., an outer radius 1 millimeter larger than an inner radius), and a thickness of about 50 micrometers. In some embodiments, the substrate 644 may encircle at least the optical area associated with the plurality of circuits 650, and may be analogous to the annular body 402. For example, the substrate 644 may be disposed in a peripheral area and in between at least two optical elements, such as optical windows 114 and 116.

In the illustrated embodiment, power supply 646 includes a battery 656 to power the various embedded electronics, including controller 648. Battery 656 may be inductively charged by charging circuitry 654 and energy harvesting antenna 652. In one embodiment, antenna 664 and energy harvesting antenna 652 are independent antennae, which serve their respective functions of energy harvesting and communications. In another embodiment, energy harvesting antenna 652 and antenna 664 are the same physical antenna that are time shared for their respective functions of inductive charging and wireless communications with reader 605. Additionally or alternatively, power supply 646 may include a solar cell ("photovoltaic cell") to capture energy from incoming ultraviolet, visible, and/or infrared radiation. Furthermore, an inertial power scavenging system can be included to capture energy from ambient vibrations.

Charging circuitry 654 may include a rectifier/regulator to condition the captured energy for charging battery 656 and/or directly power controller 648. Charging circuitry 654 may also include one or more energy storage devices to mitigate high frequency variations in energy harvesting antenna 652. For example, one or more energy storage devices (e.g., a capacitor, an inductor, etc.) can be connected to function as a low-pass filter.

Controller 648 contains control logic 658 to choreograph the operation of the other embedded components. Control logic 658 controls the general operation of ophthalmic device 600, including providing a logical user interface, power control functionality, etc. Ablation logic 660 includes logic for receiving signals from sensors monitoring one or more optical parameters of an eye into which the ophthalmic device 600 is implanted and/or program instruction 670 and manipulating the plurality of circuits 650 in response to the one or more optical parameters of the eye. More particularly, in an embodiment, ablation logic 660 includes logic that when executed by the controller 648 causes the ophthalmic device 600 to perform operations including: applying a voltage to one or more of the plurality of circuits 650 sufficient to ablate a portion of the layer 676 adjacent to the one or more of the plurality of circuits 650. As discussed further herein with respect to FIG. 4, such ablation of a portion of the layer 676 adjusts a curvature of a meniscus defined by two immiscible liquids disposed in an aperture of the ophthalmic device 600 and an optical power of the ophthalmic device 600.

Communication logic 662 provides communication protocols for wireless communication with reader 605 via antenna 664. In one embodiment, communication logic 662 provides backscatter communication via antenna 664 when in the presence of an electromagnetic field 680 output from reader 605. In one embodiment, communication logic 662 operates as a smart wireless radio-frequency identification ("RFID") tag that modulates the impedance of antenna 664 for backscatter wireless communications. The various logic modules of controller 648 may be implemented in software/firmware executed on a general purpose microprocessor, in hardware (e.g., application specific integrated circuit), or a combination of both.

Ophthalmic device 600 may include various other embedded electronics and logic modules. For example, a light source or pixel array may be included to provide visible feedback to the user.

The illustrated embodiment also includes reader 605 with a processor 672, an antenna 674, and memory 666. Memory 666 in reader 605 includes data storage 668 and program instructions 670. As shown reader 605 may be disposed outside of ophthalmic device 600, but may be placed in its proximity to charge ophthalmic device 600, send instructions to ophthalmic device 600, and/or extract data from ophthalmic device 600.

External reader 605 includes antenna 674 (or group of more than one antenna) to send and receive wireless signals 680 to and from ophthalmic device 600. External reader 605 also includes a computing system with processor 672 in communication with memory 666. Memory 666 is a non-transitory computer-readable medium that can include, without limitation, magnetic disks, optical disks, organic memory, and/or any other volatile (e.g., RAM) or non-volatile (e.g., ROM) storage system readable by the processor 672. Memory 666 can include a data storage 668 to store indications of data, such as data logs (e.g., user logs), program settings (e.g., to adjust behavior of ophthalmic device 600 and/or external reader 605), etc. Memory 666 can also include program instructions 670 for execution by processor 672 to cause the external reader 605 to perform processes specified by the instructions 670. For example, program instructions 670 can cause external reader 605 to provide a user interface that allows for retrieving information communicated from ophthalmic device 600 or allows transmitting information to ophthalmic device 600 to program or otherwise select operational modes of ophthalmic device 600. External reader 605 can also include one or more hardware components for operating antenna 674 to send and receive wireless signals 680 to and from ophthalmic device 600.

External reader 605 can be a smart phone, digital assistant, or other computing device with wireless connectivity sufficient to provide the wireless communication link 680. External reader 605 can also be implemented as an antenna module that can be plugged into a portable computing device, such as in an embodiment where the communication link 680 operates at carrier frequencies not commonly employed in portable computing devices.

In an embodiment, altering a layer, such as layers 108, 208, 308, 408, and 708, is permanent. For example, altering a layer by ablation, whether by illumination with laser light or by providing current to a circuit, is irreversible. In this regard, an optical power of such an ophthalmic device cannot be returned to an original state. However, an optical power may be further increased or decreased by, for example, further ablating an additional portion of the layer.

In an embodiment, a layer as described herein, such as layers 108, 208, 308, 408, and 708, is not altered by ambient conditions, such as ambient light including ambient sunlight or artificial lighting. Rather, as discussed further herein with respect to FIGS. 1A, 1B, 2A, and 2B, the layers described herein are altered by, for example, illumination with femto-second laser light. In this regard, an optical power of the ophthalmic device is tunable but not altered by ambient conditions such as those experienced after implantation into an eye.

Figure 5:
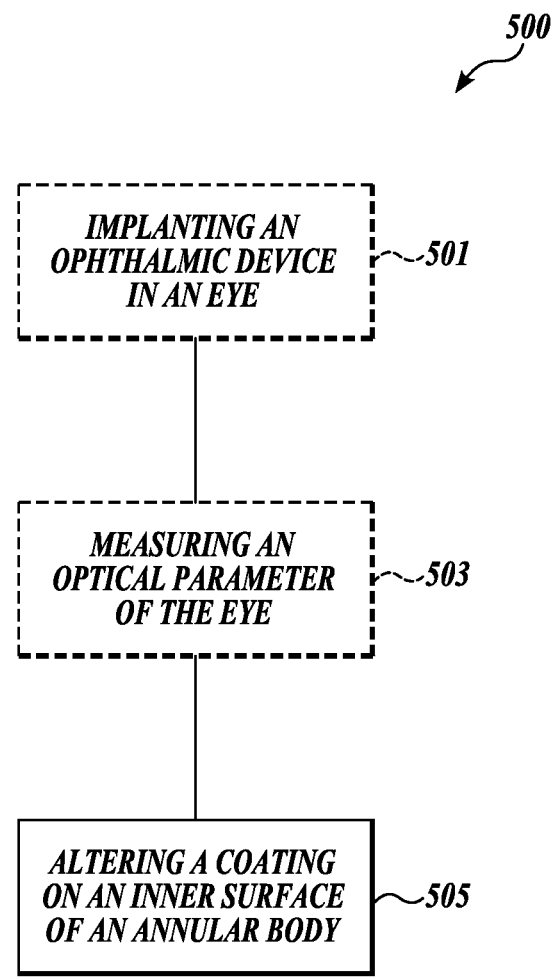
FIG. 5 illustrates a method of changing an optical power of an ophthalmic device, in accordance with an embodiment of the disclosure.

A method of changing an optical power of an ophthalmic device, such as ophthalmic devices 100, 200, 300, 400, 600, and 700, will now be described. In that regard, attention is directed to FIG. 5, which is a schematic illustration of a method 500 of changing an optical power of an ophthalmic device, in accordance with an embodiment of the disclosure. One of ordinary skill in the art having the benefit of the present disclosure will appreciate that the blocks of method 500 may occur in any order and even in parallel. Additionally, blocks may be added to, or removed from, method 500 in accordance with the teachings of the present disclosure.

The method may begin with block 505, which includes altering a layer disposed on the ophthalmic device. In an embodiment, the layer is disposed on an inner surface of an annular body of the ophthalmic device, as discussed further herein with respect to, e.g., FIGS. 1A and 1B. In an embodiment, the layer is disposed on an optical window of the ophthalmic device, as discussed further herein with respect to FIGS. 7A and 7B. In this regard, a curvature of a meniscus defined by two immiscible liquids disposed in an aperture of the annular body is altered. As discussed further herein, an optical power of a lens is defined at least in part by a curvature of such a meniscus and altering its curvature changes an optical power of the ophthalmic device.

Altering the layer may include ablating a portion of the layer. In this regard, a portion of the inner surface is newly exposed to the two immiscible liquids. As discussed further herein with respect to FIGS. 1A and 1B, ablation can include exposing the portion of the layer to laser light sufficient to ablate the portion of the layer. In an embodiment, ablating the portion of the layer with laser light includes illuminating the portion of the layer with light from a femto-second laser, such as a femto-second laser commonly used in other ophthalmological procedures such as a LASIK procedure. In an embodiment, the layer or a portion thereof is ablated while the inner surface is not ablated or at least a portion of the inner surface previously covered by the layer remains. In an embodiment, ablating the portion of the layer includes ablating the layer with a plurality of circuits embedded in the layer, as discussed further herein with respect to FIG. 4.

Altering the layer may include illuminating a portion of the layer to increase or decrease a volume of the illuminated portion of the layer. As discussed further herein with respect to FIGS. 7A and 7B, certain layer materials, such as foams and/or heat-shrink materials, can decrease in volume when illuminated with suitable laser light.

Altering the layer may further include transitioning a portion of the layer including a phase-change material from a first phase to a second phase, thereby newly exposing a portion of the inner surface, previously covered by the layer. In an embodiment, this includes illuminating the phase-change material with light, such as laser light, sufficient to transition the phase-change material from the first phase to the second phase.

As discussed further herein with respect to FIGS. 3A and 3B, alteration of the layer can be asymmetric with respect to an optical axis of the ophthalmic device, such as in the treatment of various astigmatisms. Alternatively, alteration of the layer can be symmetric with respect to the optical axis of the ophthalmic device, such as in the treatment of, e.g., myopia or hyperopia.

The method may begin with block 501, which includes implanting or mounting the ophthalmic device into or onto an eye. In this regard, the alteration of the curvature of the meniscus and change in the optical power of the ophthalmic device is performed in situ. Such implantation may be as a part of a procedure to treat, for example a cataract, myopia, hyperopia, astigmatism, or combinations thereof with an intraocular lens. Alternatively, the ophthalmic device may be mounted onto an eye, such as where the ophthalmic device is a contact lens. In an embodiment, block 501 is immediately followed by block 505.

Block 501 may be followed by block 503, which includes measuring an optical parameter of the eye including the implanted or mounted ophthalmic device. In an embodiment, an optical parameter of the eye including the implanted or mounted ophthalmic device is measured by a health care provider, such as an ophthalmologist. Further, in an embodiment, the measured optical parameter, such as an optical power of the eye including the implanted or mounted ophthalmic device, informs alteration of the layer. Accordingly, altering the layer is based at least in part on the measured optical parameter of the eye. For example, where the eye including the implanted ophthalmic device has a myopic astigmatism, the layer is altered through circularly asymmetric ablation to preferentially flatten the steepest meridian of the ophthalmic device. Similarly, where the eye including the implanted ophthalmic device has a hyperopic astigmatism, the layer is altered through circularly asymmetric ablation to preferentially steepen the flattest meridian of the ophthalmic device. Where the eye including the implanted ophthalmic device has a mixed astigmatism, the layer is altered through circularly asymmetric ablation to steepen the flattest meridian and steepen the flattest meridian of the ophthalmic device.

The order in which some or all of the process blocks appear in each process should not be deemed limiting. Rather, one of ordinary skill in the art having the benefit of the present disclosure will understand that some of the process blocks may be executed in a variety of orders not illustrated, or even in parallel.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic device comprising:
   a body including an inner surface defining an aperture through the body, wherein the inner surface includes a layer on at least a portion of the inner surface having a surface energy different than a surface energy of the inner surface; and
   two immiscible liquids disposed in the aperture defining a meniscus, wherein a curvature of the meniscus is defined at least in part by a position of an interface between the layer and the inner surface,
   wherein the ophthalmic device has a base optical power,
   wherein the layer is reconfigurable to adjust the base optical power,
   wherein the layer is wet by a first liquid of the two immiscible liquids and is not wet by a second liquid of the two immiscible liquids, and
   wherein the inner surface is wet by the second liquid and is not wet by the first liquid.

2. The ophthalmic device of claim 1, wherein the layer is configured to ablate upon illumination with laser light.

3. The ophthalmic device of claim 1, wherein the layer includes a phase-change material shaped to expose a portion of the inner surface upon transitioning from a first phase to a second phase.

4. The ophthalmic device of claim 1, further comprising:
   a plurality of circuits embedded in the layer; and
   a controller operably coupled to the plurality of circuits including logic that when executed by the controller causes the ophthalmic device to perform operations including:
   applying a voltage to one or more of the plurality of circuits sufficient to ablate a portion of the layer adjacent to the one or more of the plurality of circuits.

5. The ophthalmic device of claim 1, wherein the layer is configured to decrease in volume upon illumination with laser light.

6. The ophthalmic device of claim 1, further comprising a base lens having a static optical power coupled to the body.

7. The ophthalmic device of claim 1, wherein the curvature of the meniscus is further defined by a feature selected from the group consisting of a shape of the body, a shape of interface between the layer and the inner surface, relative volumes of the two immiscible liquids, and combinations thereof.

8. A system comprising:
   an ophthalmic device including:
      a body including an inner surface defining an aperture through the body, wherein the inner surface includes a layer on at least a portion of the inner surface having a surface energy different than a surface energy of the inner surface; and
      two immiscible liquids disposed in the aperture defining a meniscus, wherein a curvature of the meniscus is defined at least in part by a position of an interface between the layer and the inner surface, wherein the layer is wet by a first liquid of the two immiscible liquids and is not wet by a second liquid of the two immiscible liquids, and wherein the inner surface is wet by the second liquid and is not wet by the first liquid;
   a laser; and
   a controller operably coupled to the laser including logic that when executed by the ophthalmic device causes the system to perform operations including:
      illuminating a portion of the layer with laser light from the laser, wherein illuminating the portion of the layer includes illuminating the portion of the layer with laser light sufficient to ablate the portion of the layer, thereby adjusting the curvature of the meniscus defined by the two immiscible liquids.

* * * * *